United States Patent [19]

Yang et al.

[11] Patent Number: 5,254,723
[45] Date of Patent: Oct. 19, 1993

[54] PREPARATION OF GLYCOL DIESTERS FROM POLYETHERS

[75] Inventors: Lau S. Yang, Wilmington, Del.; Diane A. Macarevich, Collegeville, Pa.

[73] Assignee: ARCO Chemical Technology, L.P., Wilmington, Del.

[21] Appl. No.: 979,991

[22] Filed: Nov. 23, 1992

[51] Int. Cl.$^5$ ............................................. C07C 67/24
[52] U.S. Cl. .................................................. 560/240
[58] Field of Search ........................................ 560/240

[56] References Cited

U.S. PATENT DOCUMENTS

| | | | |
|---|---|---|---|
| 4,298,758 | 11/1981 | Cook et al. | 560/240 |
| 4,585,592 | 4/1986 | Mueller | 560/240 X |
| 4,803,299 | 2/1989 | Mueller | 560/240 |

OTHER PUBLICATIONS

*Ferric Chloride in Acetic Anhydride. A Mild and Versatile Reagent for the Cleavage of Ethers*, J. Org. Chem. vol. 39, No. 25, (1974), Bruce Ganem 2nd Vernon R. Small, Jr., pp. 3728-3730.

*Cleavage Reactions of Optically Active Secondary Butyl Methyl Ether*, Contribution from the Department of Chemistry of Northwestern University, vol. 73 pp. 2428-2431, (1951).

*The Cleavage of Ethers*, Department of Chemistry, Northwestern University, Robert L. Burwell, Jr. pp. 615-685.

*Primary Examiner*—Arthur C. Prescott
*Attorney, Agent, or Firm*—Jonathan L. Schuchardt

[57] ABSTRACT

A process for making glycol diesters from polyethers is disclosed. The polyether is reacted with an acyclic, aliphatic anhydride in the presence of a Lewis acid to produce the glycol diester. The invention provides a way to reuse polyether polyols recovered from polyurethanes by converting them to readily purified glycol diesters. The diesters are useful as solvents and as chemical intermediates.

15 Claims, No Drawings

PREPARATION OF GLYCOL DIESTERS FROM POLYETHERS

FIELD OF THE INVENTION

The invention relates to the preparation of glycol diesters, which are useful as solvents and as chemical intermediates. In particular, the invention is a process for making glycol diesters from polyethers, especially polyether polyols.

BACKGROUND OF THE INVENTION

Polyether polyols are useful intermediates for the production of polyurethanes. Polyurethanes can be transformed into aromatic amines and polyether polyols by basic hydrolysis. A largely unanswered question is how to best use polyether polyols recovered from polyurethanes. One approach is to purify and reuse the polyols, but purification is costly and often impractical. Another potential approach is to depolymerize the polyether polyol to give low molecular weight products using an ether cleavage reaction. Unfortunately, ether cleavage typically requires harsh reagents such as concentrated sulfuric acid and hydriodic acid, and is not commercially practical.

Ganum and Small (J. Org. Chem. 39 (1974) 3728) showed that aliphatic ethers react under mild conditions with acetic anhydride and ferric chloride to give esters. Aliphatic ethers also react with acid chlorides in the presence of Lewis acids to give esters, but alkyl chlorides are also produced. These reactions have apparently not been applied to polyether polyol depolymerization.

Crude polyether polyols recovered from polyurethanes usually contain many impurities. The polyols are hard to purify because of their typically high viscosities and high molecular weights. Distillation, an effective technique for purifying low molecular weight compounds, is usually not practical for polyols because of their low volatility. Of great value would be a practical way to convert polyols to low molecular weight products that are easily purified by distillation.

SUMMARY OF THE INVENTION

The invention is a process for making a glycol diester from a polyether. The process comprises reacting a polyether with an acyclic, aliphatic anhydride in the presence of an effective amount of a Lewis acid to produce the glycol diester. Particularly useful polyethers for the process are polyether polyols recovered in crude form from polyurethanes.

The process is a surprisingly practical way to convert recovered polyethers to glycol diesters, which are valuable solvents and chemical intermediates. The glycol diester is readily purified by distillation. Thus, the process of the invention provides an effective way to transform a crude polyether macromolecule into a low molecular weight glycol diester of high purity and value.

DETAILED DESCRIPTION OF THE INVENTION

The invention is a process for depolymerizing polyethers and, at the same time, a process for making glycol diesters. A polyether is reacted with an acyclic, aliphatic anhydride in the presence of a Lewis acid to produce the glycol diester.

Polyethers suitable for use in the invention are those derived from base or acid-catalyzed ring-opening polymerization of cyclic ethers such as epoxides, oxetanes, oxolanes, and the like. The polyethers have repeat units of oxyalkylene groups (-O-A-) in which A has from 2 to 10 carbon atoms, preferably from 2 to 4 carbon atoms. The polyethers can have different end groups, depending upon how they are made or modified. For example, the polyether can have hydroxyl, ester, ether, acid, or amino end groups, or the like, or combinations of these. Mixtures of different types of polyethers can be used.

Preferred polyethers useful in the process of the invention are polyether polyols. Suitable polyether polyols include, for example, polyoxypropylene polyols, polyoxyethylene polyols, ethylene oxide-propylene oxide copolymers, polytetramethylene ether glycols, oxetane polyols, and copolymers of tetrahydrofuran and epoxides. Typically, these polyols will have average hydroxyl functionalities from about 2 to about 8, and number average molecular weights from about 250 to about 25,000. Preferably, the polyether polyols are recycled polyols derived from a polyurethane foam, elastomer, sealant, or the like.

An acyclic, aliphatic anhydride is used in the process of the invention. Although any acyclic, aliphatic anhydride can be used, it it preferred for reasons of economy and effectiveness to use an acyclic $C_4$-$C_{10}$ aliphatic anhydride. Preferred anhydrides include acetic, propionic, butyric, and isobutyric anhydrides. Most preferred, because it is cheap, readily available, and gives easily distilled glycol diester products, is acetic anhydride. Mixtures of different anhydrides can be used.

The amount of acyclic, aliphatic anhydride used is usually not critical, but it is preferred to use an amount effective to convert substantially all of the ether groups in the polyether to ester groups. Thus, for a polypropylene glycol having an average of 10 oxypropylene units, for example, it is preferred to use at least about 10 moles of aliphatic anhydride per mole of polypropylene glycol. More preferably, an excess amount of the anhydride is used. The anhydride is advantageously used as a solvent; unreacted anhydride is simply separated from the glycol diester product by distillation and is recycled.

A Lewis acid catalyzes the process of the invention. Preferred Lewis acids are metal halides of the formula $MX_n$, wherein M is a metal having an oxidation number from 2 to 4, X is a halogen, and n is an integer from 2 to 4. Suitable Lewis acids include, but are not limited to, zinc chloride, zinc bromide, stannous chloride, stannous bromide, aluminum chloride, ferric chloride, boron trifluoride, and the like, and mixtures thereof. Particularly preferred are zinc halides and tin(IV) halides. Most preferred are zinc chloride and zinc bromide.

The amount of Lewis acid used is not critical. Generally, the reaction proceeds more rapidly when higher catalyst levels are used. The amount of Lewis acid used is preferably within the range of about 1 to about 50 wt. % based on the amount of polyether; a more preferred range is from about 1 to about 15 wt. %.

The process of the invention is performed by simply combining, in any desired manner or order, the polyether, anhydride, and Lewis acid, and heating the mixture to the desired reaction temperature. Although any desired reaction temperature can be used, a temperature within the range of about 60° C. to about 220° C. is generally preferred. A more preferred temperature range is from about 140° C. to about 200° C. Often, a convenient reaction temperature is the boiling point of the acyclic anhydride. For example, depolymerizations performed with acetic anhydride are conveniently performed at about 140° C., which is the approximate boiling point of acetic anhydride.

The reaction can be performed, if desired, under an inert atmosphere of nitrogen, argon, or the like, although this is not required. Preferably, the reaction is well agitated during the process.

When the reaction has reached the desired degree of completion, the products are separated by any convenient means, preferably by distillation. Any unreacted acyclic anhydride can be returned to the reactor following removal of the desired glycol diester products.

The glycol diester can be redistilled to give a product of extremely high purity and value for solvent applications. The glycol diester can also be converted easily to glycol and ester products. For example, propylene glycol diacetate reacts with methanol to give propylene glycol and methyl acetate.

The following examples merely illustrate the invention. Those skilled in the art will recognize numerous variations that are within the spirit of the invention and scope of the claims.

EXAMPLE 1

Preparation of Propylene Glycol Diacetate from Recycled Polyether Polyol--Zinc Chloride Catalyst A 250-mL, 3-neck, round-bottom flask is charged with recycled polyether polyol (30 g, recovered from a flexible slabstock polyurethane foam), and acetic anhydride (100 g). Anhydrous zinc chloride (5.0 g) is added, and the mixture is heated under reflux at 140° C. for 20 h. The condenser is removed, and a distillation head is attached. Unreacted acetic anhydride is removed by distillation. Propylene glycol diacetate is then collected at 120° C., 20 mm. Yield: 69 g (83%). Gas chromatography shows that the product is identical to an authentic sample of propylene glycol diacetate. The product structure is also confirmed by proton and $^{13}C$ NMR spectroscopies.

EXAMPLE 2

Preparation of Propylene Glycol Diacetate from Recycled Polyether Polyol--Ferric Chloride Catalyst The procedure of Example 1 is followed, except that ferric chloride (5.0 g) is used in place of zinc chloride. The yield of propylene glycol diacetate is 10 g (12%).

EXAMPLE 3

Preparation of Propylene Glycol Diacetate from 3000 Mol. Wt. Polyether Triol--Zinc Chloride Catalyst A 1-liter flask is charged with 3000 mol. wt. polyether triol (200 g, PO/EO copolymer having about 15 wt. % internal oxyethylene content; a flex-slab polyol), acetic anhydride (500 g), and zinc chloride (35 g). The mixture is heated to 140° C. for 7 h. Propylene glycol diacetate is isolated by distillation in 80% yield.

EXAMPLES 4-8 AND COMPARATIVE EXAMPLES 9-12

Effect of Catalyst on Depolymerization of Polyether Polyols

A 250-mL, 3-neck, round-bottom flask is charged with 3000 mol. wt. polyether triol (20 g, see Ex. 3), acetic anhydride (40 g), and a catalyst (1 g, see Table 1). The mixtures are refluxed for 6 h, and the products are analyzed by gas chromatography. Yields appear in Table 1.

These depolymerization experiments show that Lewis acid catalysts are needed, and zinc halides are most effective.

EXAMPLE 13

Depolymerization of Polyethylene Glycol Using Acetic Anhydride and Ferric Chloride A 250-mL, 3-neck, round-bottom flask is charged with 600 mol. wt. polyethylene glycol (10 g), acetic anhydride (40 g), and ferric chloride (3.5 g). The mixture is heated under reflux (140° C.) for 2 h. Analysis by gas chromatography shows a 12% yield of ethylene glycol diacetate.

EXAMPLE 14

Depolymerization of Polyethylene Glycol Using Acetic Anhydride and Zinc Chloride The procedure of Example 13 is followed with 2.5 g of zinc chloride in place of ferric chloride. After 2 h, the yield of ethylene glycol diacetate is less than 10%.

EXAMPLE 15

Depolymerization of Polytetramethylene Ether Glycol (PTMEG) Using Acetic Anhydride and Zinc Chloride A 100-mL flask is charged with 1000 mol. wt. PTMEG (5.0 g), acetic anhydride (32 g), and zinc chloride (1.0 g). The mixture is refluxed for 4 h at 140° C. Tetramethylene glycol diacetate is obtained in 31% yield.

The preceding examples are only illustrations; the true metes and bounds of the invention are defined by the following claims.

TABLE 1

| Effect of Catalyst on Depolymerization of Polyether Polyols | | |
|---|---|---|
| Example # | Catalyst | Propylene Glycol Diacetate (% Yield) |
| 4 | aluminum chloride | 1 |
| 5 | ferric chloride | 7 |
| 6 | stannous chloride | 8 |
| 7 | zinc chloride | 29 |
| 8 | zinc bromide | 32 |
| C9 | ferrous sulfate | 0 |
| C10 | zinc acetate dihydrate | 0 |
| C11 | zinc oxide | 0 |
| C12 | zinc stearate | 0 |

C - denotes comparative example
Reaction conditions: 1 g catalyst/20 g polyether triol (3000 mol. wt.); 6 h, 140° C. Yields by gas chromatography.

We claim:

1. A process for making a glycol diester from a polyether, said process comprising reacting the polyether with an acyclic, aliphatic anhydride in the presence of an effective amount of a Lewis acid to produce the glycol diester.

2. The process of claim 1 wherein the polyether is a polyether polyol selected from the group consisting of polyoxypropylene polyols, polyoxyethylene polyols, ethylene oxide-propylene oxide copolymers, polytetramethylene ether glycols, oxetane polyols, and copolymers of tetrahydrofuran and epoxides.

3. The process of claim 1 wherein the acyclic anhydride is a $C_4$-$C_{10}$ acyclic, aliphatic anhydride.

4. The process of claim 1 wherein the acyclic anhydride is acetic anhydride.

5. The process of claim 1 wherein the Lewis acid is a metal halide of the formula $MX_n$, wherein M is a metal having an oxidation number from 2 to 4, X is a halogen, and n is an integer from 2 to 4.

6. The process of claim 1 wherein the Lewis acid is selected from the group consisting of zinc halides and tin(IV) halides.

7. The process of claim 2 wherein the polyether polyol is a recycled polyol from a polyurethane product.

8. A process for making a glycol diester from a polyether polyol, said process comprising reacting the polyether polyol with acetic anhydride in the presence of an effective amount of a Lewis acid to produce the glycol diester.

9. The process of claim 8 wherein the polyether polyol is selected from the group consisting of polyoxypropylene polyols, polyoxyethylene polyols, ethylene oxide-propylene oxide copolymers, polytetramethylene ether glycols, oxetane polyols, and copolymers of tetrahydrofuran and epoxides.

10. The process of claim 8 wherein the Lewis acid is a metal halide of the formula $MX_n$, wherein M is a metal having an oxidation number from 2 to 4, X is a halogen, and n is an integer from 2 to 4.

11. The process of claim 8 wherein the Lewis acid is selected from the group consisting of zinc halides and tin(IV) halides.

12. The process of claim 8 wherein the polyether polyol is a recycled polyol from a polyurethane product.

13. A process for making a glycol diester from a polyether polyol, said process comprising reacting a polyether polyol selected from the group consisting of polyoxypropylene polyols, polyoxyethylene polyols, ethylene oxide-propylene oxide copolymers, polytetramethylene ether glycols, oxetane polyols, and copolymers of tetrahydrofuran and epoxides, with acetic anhydride in the presence of an effective amount of a Lewis acid of the formula $MX_n$, wherein M is a metal having an oxidation number from 2 to 4, X is a halogen, and n is an integer from 2 to 4, to produce the glycol diester.

14. The process of claim 13 wherein the Lewis acid is selected from the group consisting of zinc halides and tin(IV) halides.

15. The process of claim 13 wherein the polyether polyol is a recycled polyol from a polyurethane product.

* * * * *